United States Patent
Richard

[11] Patent Number: 5,944,677
[45] Date of Patent: Aug. 31, 1999

[54] VARIABLY ADJUSTABLE LIMB IMMOBILIZER

[76] Inventor: Patricia A. Richard, 100 Sandpiper Cir., Milford, Conn. 06460

[21] Appl. No.: 09/004,281

[22] Filed: Dec. 30, 1997

Related U.S. Application Data

[60] Provisional application No. 60/024,815, Dec. 31, 1996.
[51] Int. Cl.[6] .................................. A61F 5/00; A61F 5/37
[52] U.S. Cl. .................................. 602/23; 602/5; 128/877
[58] Field of Search ..................................... 128/877, 878, 128/882, 892; 602/5, 12, 20, 23, 27, 32, 36, 38; 5/650, 651, 648; 269/203, 296, 299, 164; 248/298.1, 230.3, 230.6, 70

[56] References Cited

U.S. PATENT DOCUMENTS

| | | | |
|---|---|---|---|
| 570,085 | 10/1896 | Clausson | 602/5 |
| 2,697,436 | 12/1954 | Coston | 128/877 |
| 4,181,297 | 1/1980 | Nichols | 5/650 |
| 4,373,709 | 2/1983 | Whitt | 5/650 |
| 4,647,028 | 3/1987 | Yang | 269/164 X |
| 4,996,977 | 3/1991 | Tiedeken | 128/878 |
| 5,042,508 | 8/1991 | Richard | 128/882 |

*Primary Examiner*—Richard J. Apley
*Assistant Examiner*—Denise Pothier

[57] ABSTRACT

Patients' limb immobilizers for stabilizing fractured or broken limbs, which may be enclosed in casts, are structured to eliminate rolling movement of the limb, to promote comfort and healing. Laterally extending support bases resting on a bed or other underlying support surface are provided with a pair of upwardly-extending limb-embracing elements, which are adjustable to provide close embrace of the patient's limb. The elements may be rigid or flexible; they are releasably clamped on the patient's limb for optimum immobilization.

11 Claims, 3 Drawing Sheets

VARIABLY ADJUSTABLE LIMB IMMOBILIZER

This application claims the benefit of U.S. Provisional Application No. 60/024,815, filed Dec. 31, 1996.

This invention relates to limb immobilizers for positioning and stabilizing patients' fractured or broken limbs, and particularly to portable support devices for stabilizing an injured extremity enclosed in a cast to promote healing.

BACKGROUND OF THE INVENTION

My U.S. Pat. No. 5,042,508 describes a related device with flexible support arms for embracing the user's cast-enclosed extremity, with padded lining secured to the interior support arm surfaces to reduce pressure points and prevent irritation of the user's skin or damaging of the cast when the limb engaging arms are supporting them.

The device of this invention provides desirable adjustability for the space between the juxtaposed support arms and for the longitudinal space between the support units themselves if two or more are arrayed along the length of the user's limb.

BRIEF SUMMARY OF THE INVENTION

As shown in the figures, the invention comprises two or more support bases with upstanding arcuate support arms adjustably mounted thereon for movement toward and away from each other to the desired adjusted positions. In addition, two or more of these support base units may be spaced apart by slotted attachment bars, which are also adjustably anchored to the support units to change the spacing along the user's limb.

Accordingly, the principal object of the present invention is to achieve the advantages of my device disclosed in my U.S. Pat. No. 5,042,508 while also providing lateral adjustability in the clasping engagement of the user's limb or cast, as well as longitudinal adjustability of the spacing between support units, if desired.

Another object is to provide supple and flexible bands for embracing the immobilized limb, offering variable clamping embrace accommodating limbs and casts of widely different size and shape.

Other objects of the invention will in part be obvious and will in part appear hereinafter.

The invention accordingly comprises the features of construction, combinations of elements, and arrangement of parts which will be exemplified in the construction hereinafter set forth, and the scope of the invention will be indicated in the claims.

THE DRAWINGS

For a fuller understanding of the nature and objects of the invention, reference should be made to the following detailed description taken in connection with the accompanying drawings, in which.

BEST MODE FOR CARRYING OUT THE INVENTION

Figure 3:
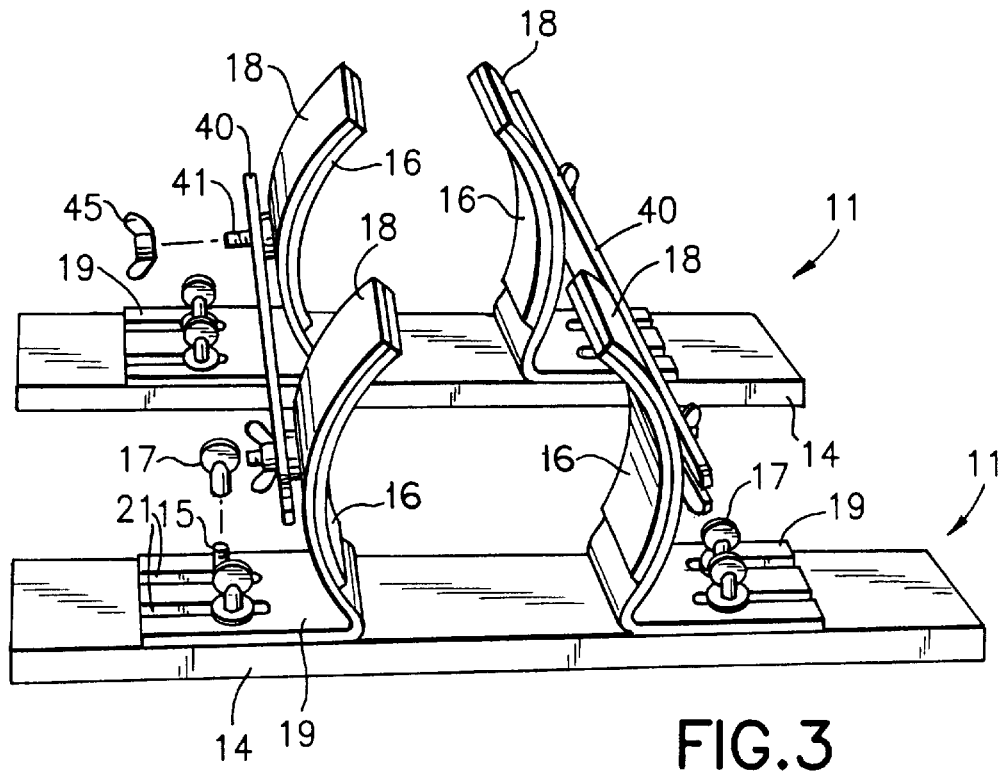
FIG. 3 is an end perspective view showing the device of the present invention.

The limb immobilizing devices of this invention generally indicated at 11 each incorporate a support base unit 14 which is formed of metal, or of bars of wood, in this embodiment of the device. Upstanding from the upper surfaces of the support bases 14 near their ends are pairs of upstanding threaded studs 15, one of which is shown in FIG. 3, on which internally threaded torque keys 17 are engaged. Clamped to each support base 14 by the cooperation of keys 17 threadedly engaged on studs 15 are facing pairs of support arms 18 having a soft resilient layer of padded lining 16 mounted on their facing inner surfaces. Arms 18 are provided with slotted base plates 19 each provided with two laterally outward opening slots 21 slidingly engageable on studs 15, as best shown in FIG. 3.

As shown in the figures, the laterally outwardly projecting base plate 19 of each of the support arms 18 is thus adapted for sliding movement back and forth toward and away from its end of the support base 14. Formed at the inner end of each slidable base plate 19 is the upwardly projecting curved portion of the support arm 18, formed with a convex outward facing curve, with the resulting concave inner surface supporting the padding 16 and facing the juxtaposed padding 16 on the concave inner surface of the opposite support arm 18 mounted at the other end of the support base 14, with its slots 21 securing its base plate 19 in an adjusted position on the support base 14.

The adjustability provided by studs 15, keys 17 and slotted base plates 19 with slots 21 thus allows the pair of support arms 18 to be moved apart to accommodate the insertion of the user's limb or cast, and then to be moved toward each other to clamp and immobilize the limb or the cast in the position desired, after which the torque keys 17 are tightened on studs 15 and the entire support unit 11 thus becomes a unitary structure.

Lengthwise Adjustability

When two or three of the support units 11 are to be arrayed along the length of the user's limb, attachment bars 40 are employed to adjust the position of the units 11 along the limb and then to clamp them firmly in position. This is achieved by threaded studs 41 protruding outward from a central portion of the convex outer surface of each support arm 18 to receive and engage a slot 43 formed in each end of each attachment bar 40 spanning the longitudinal distance between the two units 11, as shown in the drawings.

Figure 2:
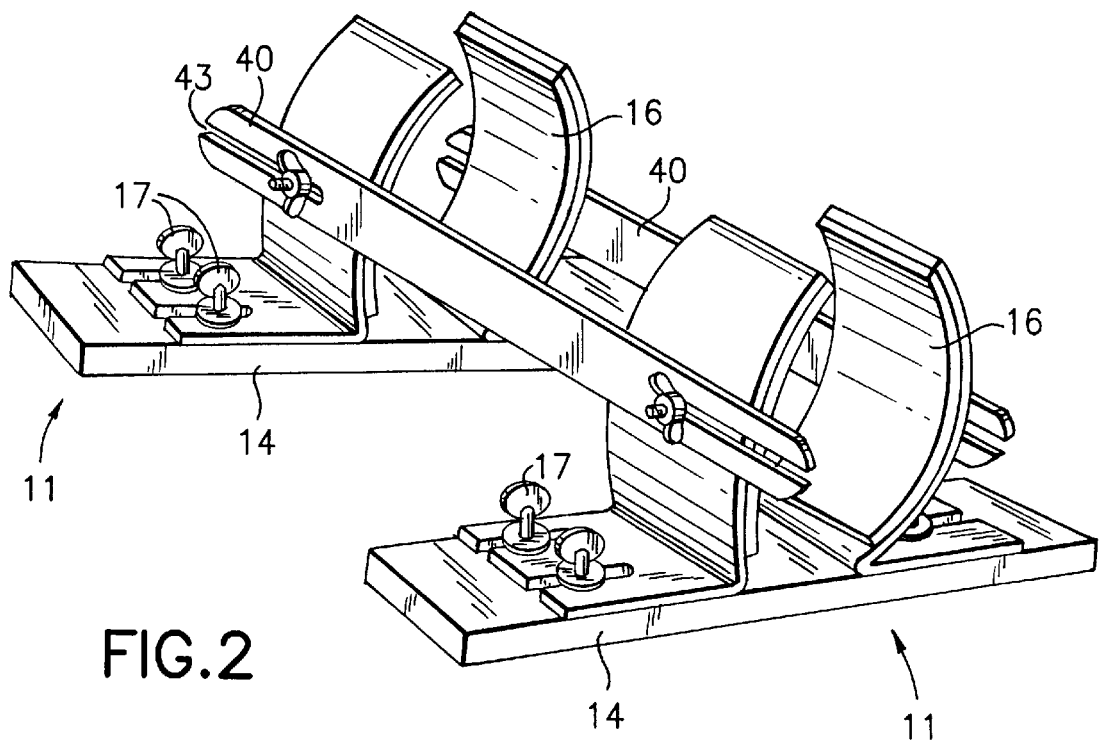
FIG. 2 is a diagonal perspective view of the same embodiment.

A wing nut 45, engageable on each threaded stud 41, clamps the unit 11 to the bar 40 in the desired adjusted position, which may be close to the blind end of slot 43 as shown at the right end of FIG. 2, or midway along the slot 43 as shown at the left end of FIG. 2. A second slotted bar 40 may be overlapped beside the first bar 40 on the stud 41, to position a third support unit 11 at the desired longitudinal distance for additional support of the user's limb.

Figure 4:
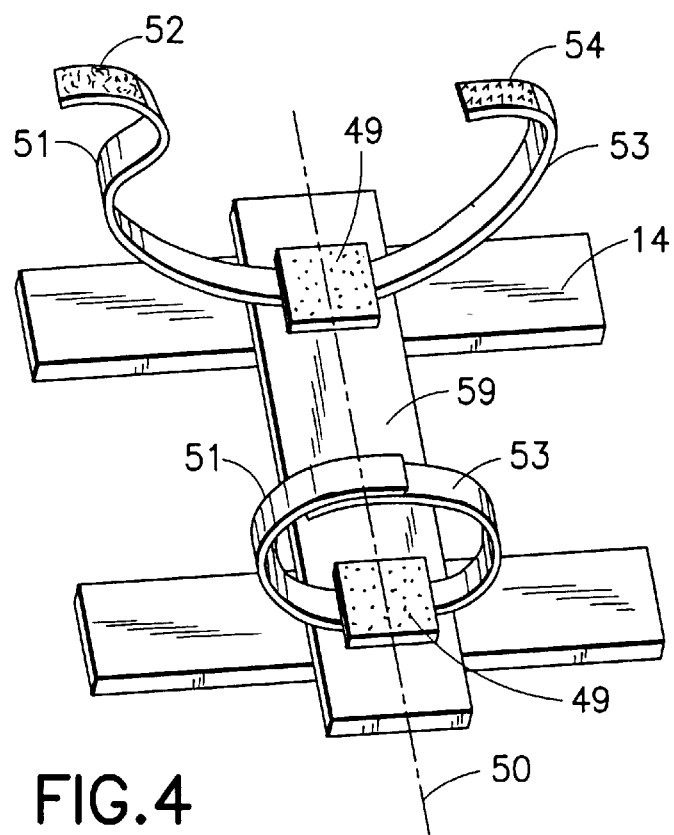
FIG. 4 is a top perspective view of a second embodiment of the present invention.
Figure 5:
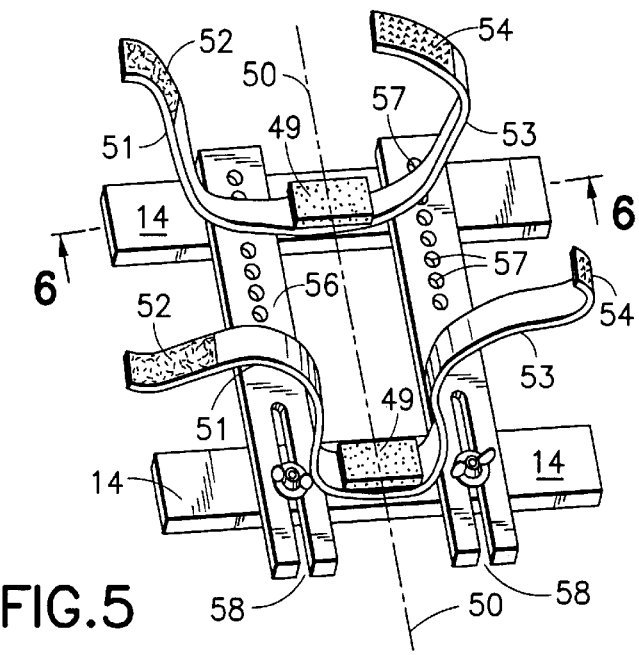
FIG. 5 is a top perspective view of a third embodiment of the present invention.
Figure 6:
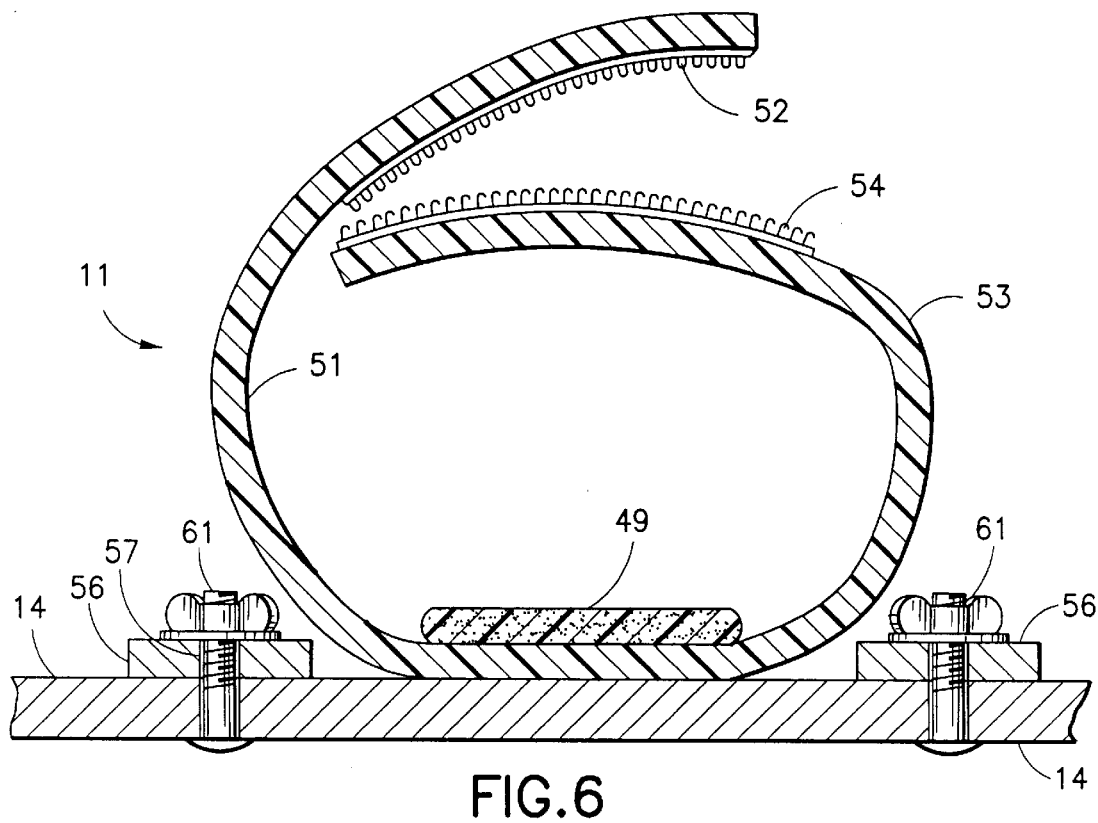
FIG. 6 is a sectional end elevation view of the embodiment of FIG. 5, taken along plane 6—6 shown in FIG. 5.

FIGS. 4, 5 and 6 show different embodiments of the invention, providing fixed or variable longitudinal spacing between support units, and a long, supple, flexible band centrally secured to the upper side of each support unit, with its opposite ends extending laterally as a pair of flexible limb embracing support bands. These bands are preferably formed of leather, rubber or elastomer, presenting straps which are mounted on each support unit, with adjustably interlocking ends. A soft, depressible foam pad 49 is preferably secured to the upper limb-supporting surface of each support band at its central region (FIGS. 4,5), to cushion the patient's arm or leg during use. Similar bands, preferably interlocked with VELCRO® hook-and-loop area fasteners, are shown in FIGS. 4, 5 and 6.

In all of these three FIGURES, the flexible support bands 51 extend to the left from the longitudinal centerlines 50 of the immobilizer 11, and incorporate an inward facing terminal area patch 52 of fastener loop units. Likewise, cooperating flexible support bands 53 extend to the right from the centerlines 50 of the support units 11, each carrying at their outer ends an outward facing terminal patch of fastener hook units 54. The terminal fastener area patches extend sufficiently far from the distal ends of the flexible straps 51 and 53 to provide a wide range of overlapped fastened positions, adapting the device to provide a tight anchored embrace for patients' limbs large and small, whether immobilized in a cast, or merely bandaged or splinted. Larger sizes of the device accommodate knee and thigh casts, while smaller sizes are used for forearm, upper arm and lower leg casts. If the caregiver prefers to reverse the positions of the hook patch 54 and the loop patch 52, the devices of FIGS. 4 and 5 may simply be reversed, end for end, to achieve this result.

Figure 1:
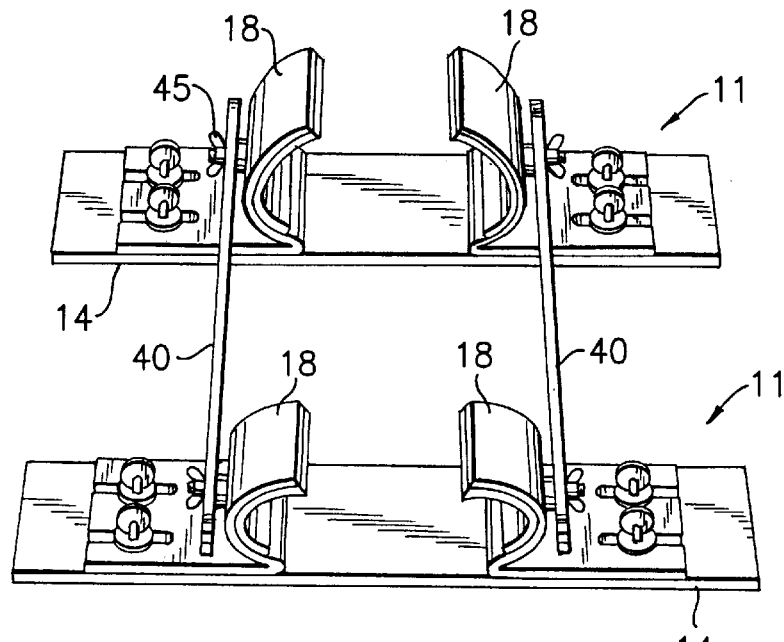
FIG. 1 is a top perspective view showing a first embodiment of the present invention.

The lateral clamping adjustability accommodating different sizes and shapes of casts, provided by the slots 21 and fastenings 15 and 17 in the devices of FIGS. 1, 2 and 3, is provided in the devices of FIGS. 4 and 5 by the infinite variability of positioning of the VELCRO® hook and loop area fasteners before engagement of patches 52 and 54.

The longitudinal adjustability which allows positioning of the support bases closer together or farther apart along the patient's limb, provided by the slots 43 in attachment bars 40 and the studs 41 and wing nuts 45 in the devices of FIGS. 1, 2 and 3, can be matched by longitudinal base bars 56 having a selection of adjustment holes 57 or longitudinal slots 58, for removable bolted attachment to base 14 via wing nut-and-bolt assemblies 61, (FIG. 6) or by detachable snap fasteners.

If the wide lateral adjustability of the flexible clamping bands 51 and 53 makes unnecessary the longitudinal adjustment of the spacing between support units 14, then the device shown in FIG. 4 provides an economical assembly. This employs a central base plate 59 fixedly anchored to both laterally extending support bases 14 at their preferred spaced-apart position. Central plate 59 and support bases 14 may be formed of wood, aluminum or stainless steel, or sturdy molded polymers, and the various embodiments of the invention shown in FIGS. 1–6 thus provide a long useful life, coupled with widely varying adjustability in the size and shape of patients' limbs and casts which they can immobilize to promote patients' comfort and healing.

It will thus be seen that the objects set forth above, and those made apparent from the preceding description, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A patient's limb positioning and stabilizing device comprising:

two transverse substantially flat rigid support bases, each adapted to have a lateral length substantially greater than the diameter of the patient's limb, and having an upper limb supporting surface and a flat lower face adapted to rest upon an underlying surface, spacing means joining the two support bases and positioning them spaced a predetermined longitudinal distance apart along the limb, a pair of upwardly extending first and second limb-embracing elements movably mounted on the upper limb-supporting surface of each base facing each other and flanking a central region of said upper surface, adjustment means for movably positioning said limb-embracing elements relative to said support base and to the patient's limb to provide abutting embrace of limb between said elements, and releasable clamping means for anchoring said limb-embracing elements in said abutting embrace of the limb, and for releasing and re-anchoring said embrace when desired, whereby the limb is supported above said upper limb supporting surfaces at two spaced apart locations and is stabilized against longitudinal and rotational movement.

2. The stabilizing device of claim 1, wherein each element of the pairs of limb-embracing elements comprises:

a base plate slidingly mounted on said support base for adjustable movement toward and away from the base plate of the second element of the pair, and a support arm projecting upward from the base plate and concavely curved facing the support arm of the second element of the pair.

3. The device of claim 2 wherein the curved support arms each have a soft resilient layer of padded lining mounted on their concavely facing inner surfaces.

4. The device of claim 2 wherein the base plate of each element is provided with laterally extending slot means for slidable engagement with upstanding fastening means protruding upward through said slot means for adjustment of the lateral spacing between the pairs of support arms.

5. The stabilizing device of claim 2 wherein said spacing means comprises rigid longitudinally extending attachment bar means having a first end adjustably and removably anchored to one support base of said device, and a second end adjustably and removably anchored to the second support base of said stabilizing device, whereby said concavely curved support arms of each pair of limb-embracing elements may be independently adjusted for lateral clamping of a patient's limb at two adjustably spaced longitudinal positions, with the spacing between the facing support arms of each pair being independently adjustable.

6. The stabilizing device of claim 5 wherein the spacing attachment bar means are joined to each support base by adjustable and removable fasteners.

7. The stabilizing device of claim 5 wherein the spacing attachment bar means are joined to each support base by adjustable fasteners removably anchoring said bar means to a support arm of one of the limb-embracing elements mounted on the upper surface of said support base.

8. The limb stabilizing device defined in claim 1, wherein each pair of upwardly extending limb-embracing elements are formed as opposite ends of a laterally extending flexibly deformable flat band having a central portion firmly anchored to a central region of the upper surface of said support base, said opposite ends being provided with said releasable clamping means.

9. The limb stabilizing device of claim 8, wherein the clamping means comprise infinitely adjustable mating areas of hook-and-loop area fasteners positioned at overlapping ends of said band, whereby the patient's limb is clampingly hugged by a continuously embracing flexible band, which can be released by peeling open the area fasteners whenever required.

10. The device of claim 8, further including a soft resilient layer of padded lining secured to the central portion of each flat band facing the patient's limb.

11. The stabilizing device of claim 8, wherein said spacing means comprises a rigid, longitudinally extending central base plate having a first end fixedly anchored to a first one of said support bases between a central region thereof and the central portion of the flat band anchored thereto and having a second end fixedly anchored to the second support base spaced apart from said first support base of the stabilizing device between a central region of said second support base and the central portion of the flat band anchored thereto, whereby the support bases and their flexibly-deformable limb-embracing band ends are anchored in the desired longitudinally spaced-apart relationship.

* * * * *

UNITED STATES PATENT AND TRADEMARK OFFICE
CERTIFICATE OF CORRECTION

PATENT NO. : 5,944,677
DATED : August 31, 1999
INVENTOR(S) : Patricia A. Richard It is certified that error appears in the above-indentified patent and that said Letters Patent is hereby corrected as shown below:

Column 4, line 15, before "limb" (second occurrence)
--the-- should be inserted

Signed and Sealed this

Twenty-fourth Day of October, 2000

Q. TODD DICKINSON

Attest:

*Attesting Officer*                *Director of Patents and Trademarks*

UNITED STATES PATENT AND TRADEMARK OFFICE
CERTIFICATE OF CORRECTION

PATENT NO. : 5,944,677  
DATED : August 31, 1999  
INVENTOR(S) : Patricia A. Richard Page 1 of 1

It is certified that error appears in the above-identified patent and that said Letters Patent is hereby corrected as shown below:

Title page,
Before Item [57], ABSTRACT, insert:

[74]    Attorney, Agent, or Firm --

Ware Fressola Van Der Sluys & Adolphson LLP

Signed and Sealed this

Fifth Day of February, 2002

Attest:

JAMES E. ROGAN
Attesting Officer    *Director of the United States Patent and Trademark Office*